United States Patent
Hall

(10) Patent No.: US 8,439,919 B2
(45) Date of Patent: May 14, 2013

(54) IMPLANT PROVIDED WITH ATTACHMENT AND HOLE-INSERT PARTS, AND A METHOD FOR PRODUCING SUCH AN IMPLANT

(75) Inventor: Jan Hall, Gothenburg (SE)

(73) Assignee: Nobel Biocare Services AG, Zurich-Fluhafen (CH)

( * ) Notice: Subject to any disclaimer, the term of this patent is extended or adjusted under 35 U.S.C. 154(b) by 640 days.

(21) Appl. No.: 12/634,466

(22) Filed: Dec. 9, 2009

(65) Prior Publication Data

US 2010/0159418 A1 Jun. 24, 2010

Related U.S. Application Data

(63) Continuation of application No. 10/240,549, filed as application No. PCT/SE01/00728 on Apr. 3, 2001, now abandoned.

(30) Foreign Application Priority Data

Apr. 4, 2000 (SE) ...................................... 0001202

(51) Int. Cl.
  *A61B 17/56* (2006.01)
  *A61B 17/58* (2006.01)
  *A61F 2/30* (2006.01)

(52) U.S. Cl.
  USPC .............................. 606/76; 606/300; 606/309

(58) Field of Classification Search .................. 606/300, 606/301, 315
See application file for complete search history.

(56) References Cited

U.S. PATENT DOCUMENTS

| | | | |
|---|---|---|---|
| 4,351,069 A | | 9/1982 | Ballintyn et al. |
| 4,463,753 A | | 8/1984 | Gustilo |
| 4,542,539 A | * | 9/1985 | Rowe et al. ................. 623/23.57 |
| 4,564,429 A | | 1/1986 | Depiereux |
| 4,801,300 A | | 1/1989 | Kurze et al. |
| 4,959,054 A | | 9/1990 | Heimke et al. |
| 4,976,739 A | | 12/1990 | Duthie, Jr. |
| 5,152,794 A | | 10/1992 | Davidson |

(Continued)

FOREIGN PATENT DOCUMENTS

| | | |
|---|---|---|
| SE | 9901971-3 | 12/2000 |
| SE | 9901973-9 | 12/2000 |
| SE | 9901974-7 | 12/2000 |
| WO | WO-9932204 A2 | 7/1999 |

OTHER PUBLICATIONS

U.S. Appl. No. 10/240,549, filed Apr. 17, 2003, Manning.

*Primary Examiner* — Andrew Yang
(74) *Attorney, Agent, or Firm* — Novak Druce Connolly Bove + Quigg LLP

(57) ABSTRACT

An implant (4) is provided with attachment and hole-insert parts (2, 3) with surfaces which have different degrees of finishing and/or degrees of roughness and/or porosities (2*f*, 2*g*). Arranged on the surfaces there is at least one dozen (A-B) in which the degree of finishing and/or the degree of roughness and/or the porosity is continuously changed. The changes in porosity in said zones can mirror continuous or discontinuous changes in the bone in question, for example the jaw bone or tooth bone. The continuously changed zones can be obtained with the aid of electrolyte (15) and, connected to the latter, an anode and cathode arrangement (13, 14). When establishing the porosity, it is possible to mask different portions of the respective implant and to control the temperature of the implant.

16 Claims, 5 Drawing Sheets

U.S. PATENT DOCUMENTS

| | | |
|---|---|---|
| 5,181,850 A | 1/1993 | Neumeyer |
| 5,205,921 A | 4/1993 | Shirkanzadeh |
| 5,211,833 A | 5/1993 | Shirkhanzadeh |
| 5,259,398 A | 11/1993 | Vrespa |
| 5,478,237 A | 12/1995 | Ishizawa |
| 5,489,306 A * | 2/1996 | Gorski ................ 623/23.55 |
| 5,503,558 A | 4/1996 | Clokie |
| 5,702,695 A | 12/1997 | Clokie |
| 5,736,152 A | 4/1998 | Dunn |
| 5,871,486 A | 2/1999 | Huebner et al. |
| 5,885,079 A | 3/1999 | Niznick |
| 5,915,967 A | 6/1999 | Clokie |
| 5,934,287 A | 8/1999 | Hayashi et al. |
| 6,027,742 A | 2/2000 | Lee et al. |
| 6,183,255 B1 | 2/2001 | Oshida |
| 6,301,418 B1 | 10/2001 | Freier et al. |
| 6,689,170 B1 | 2/2004 | Larsson et al. |

* cited by examiner

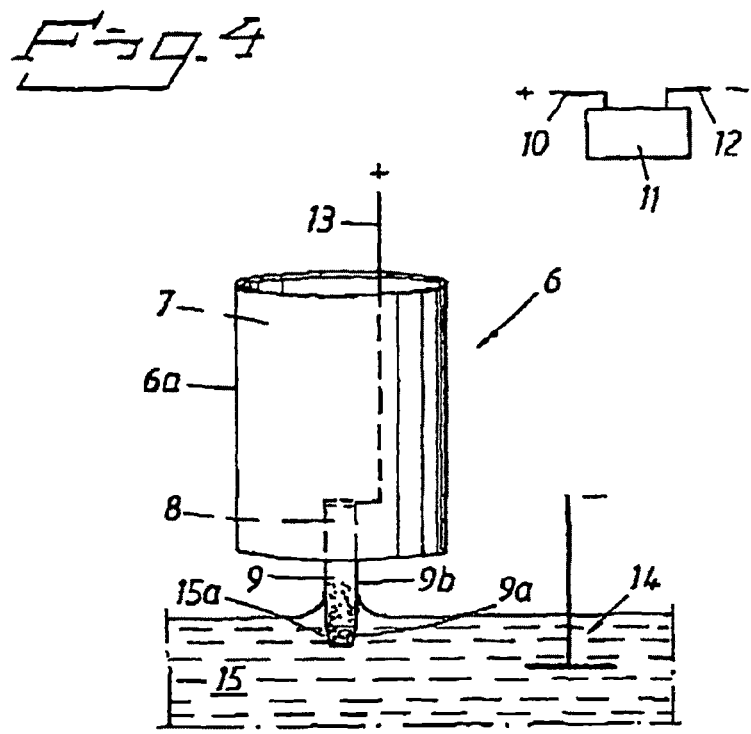
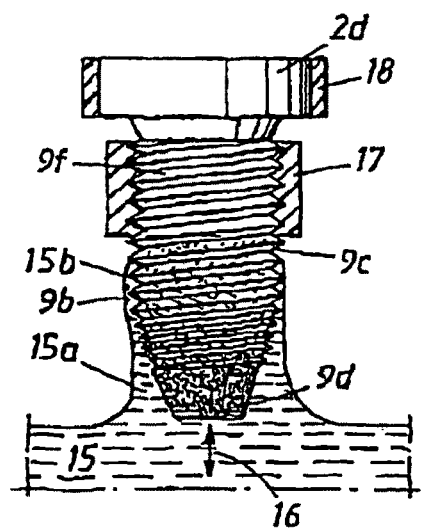

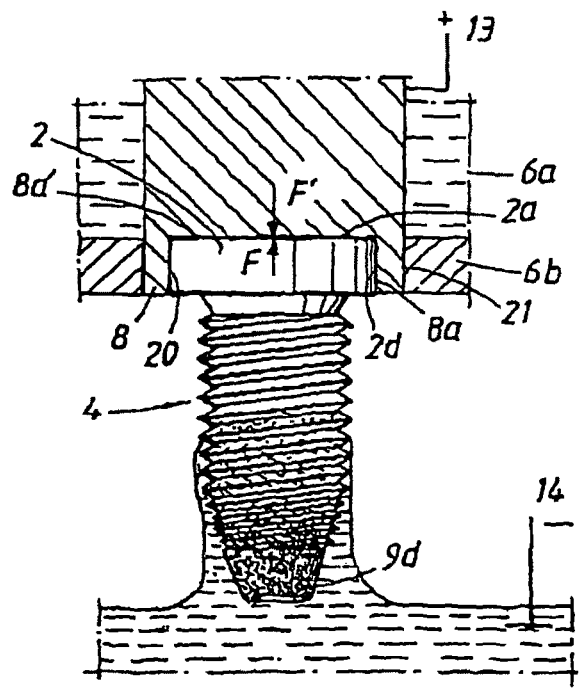
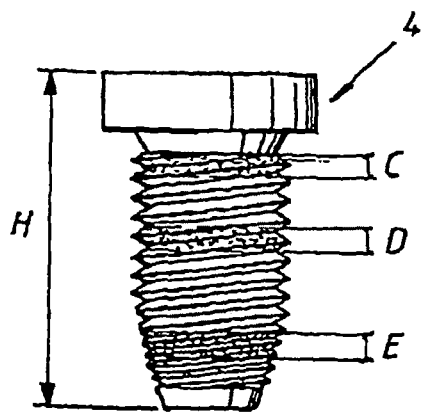
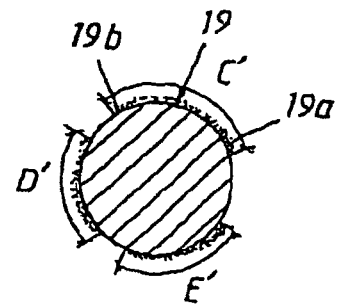

IMPLANT PROVIDED WITH ATTACHMENT AND HOLE-INSERT PARTS, AND A METHOD FOR PRODUCING SUCH AN IMPLANT

CROSS-REFERENCE APPLICATION

The present application is a continuation application of U.S. application Ser. 10/240,549, filed on Apr. 17, 2003. U.S. application Ser. No. 10/240,549 is a national stage of PCT/SE2001/000728, filed on Apr. 3, 2001, which claims priority from Sweden application 0001202-1, filed Apr. 4, 2000. The entire contents of these applications are fully incorporated herein by reference.

BACKGROUND

The present invention relates to an implant provided with attachment and hole-insert parts which have surfaces with different degrees of finishing and/or degrees of roughness and/or porosities. It also relates to a method for establishing different degrees of finishing and/or degrees of machining and/or porosities on outer surfaces of an implant with attachment and hole-insert parts. The invention also relates to an arrangement for providing a range of implants which are optimized for different dental situations.

It is already known to use implants which have upper parts for attachment of spacer elements or other superstructures and, below said upper parts, lower parts which are intended to be inserted in a hole in the bone, for example in the jaw bone or tooth bone. The attachment part in question is arranged on the jaw bone which, after the implant has become incorporated, is exposed for connection of the spacer or superstructure in question. Said lower parts can be designed with threads and it is possible to use straight cylindrical thread portions which at the bottom merge into a cone-shaped threaded portion at the tip of the implant.

For examples of implants, reference may be made inter alia to WO 97/43976 and WO 97/03621.

It is, also already known to provide the different surfaces of the implant with different finishes and/or machine treatments and/or porosities. In this connection reference may be made to, inter alia, the Swedish applications 9901971-3, 9901973-9 and 9901974-7 filed by the same applicant as the present application. Reference may also be made to U.S. Pat. Nos. 5,571,017, 5,829,978, 5,842,865, 5,885,079, 5,947,735 and 5,989,027.

From the above references it is already known to use different degrees of porosity on the surfaces in question. There are different opinions concerning the sizes of the pores and their applications. Thus, it has previously been proposed that the surface of the attachment part be made of a machined smooth surface, while the threads on the lower parts of the implant can be made with porosities of different sizes, i.e. different degrees of roughness. From the above references it is also already known to provide different parts along the longitudinal extent of the implant with different degrees of porosity. It is known that one zone with a first degree of porosity on the surface changes abruptly into a second or adjacent zone having a second degree of porosity.

SUMMARY

In the case of implants, for example in dentistry, it is preferable to avoid abrupt changes between different zones with different degrees of porosity and instead provide one or more marked or extended zones in which the change of porosity is continuously modified. Thus, in a marked or extended zone, a first porosity can be present at one end of the zone and can condense or decrease towards the other end of the zone. In one embodiment, the zone in question will be able to extend along at least the greater part of the longitudinal extent of the implant. Thus, for example, a porosity of zero, or close to zero, will be present on the surface at the attachment part of the implant, i.e. the degree of finishing and/or degree of machining is high on this surface. Thereafter, i.e. on the surface of the thread(s) of the implant, the porosity will start with a low value and will increase gradually in the longitudinal direction of the implant towards the tip of the implant, or vice versa. The increase in the porosity of the implant along the longitudinal extent of the implant can be made linear or progressive. Implants will alternatively be able to be provided with two or more such marked zones where the porosity is linearly or progressively increasing or decreasing from one end of the respective zone to the other end of the zone. In a further alternative embodiment, the porosity or the porosities will be able to increase linearly or progressively in the circumferential directions of the implant. In a further alternative, the porosities will be able to form marked islands on the outer surfaces of the implant, which islands are thus situated on finished and/or machined surfaces.

The variations in the degrees of finishing and/or machining and/or the porosities will be able to meet different requirements of dental situations, for example, where implants must be able to be applied in different types of bone, for example tooth bone and jaw bone in the upper jaw, tooth bone and jaw bone in the front and inner areas of the lower jaw, etc. The porosities must be able to provide different possibilities of introducing or anchoring the implant in tooth bones or jaw bones of different degrees of softness or hardness. In some cases the porosities are also intended to be used as depots for bone-growth-stimulating or bone-growth-promoting agents, and the movement of these agents from the depots to the surrounding bone must be controlled and varied according to the different dental situations. The porosities must therefore be able to mirror the tooth bone structure and provide optimum insertion and anchoring functions for the implant in the respective bone and optimum functions concerning the release of the bone-growth-stimulating agents.

There is therefore a need to be able to provide implants with optimum porosities, and the continuous or soft transitions in the marked zones are dictated by the fact that the changes or differences in the different bone types or bone conditions consist of indistinct transitions or changes, i.e. the hardness or softness of a bone's structure often represents a soft or continuous change in the patient's jaw bone or tooth bone. From the purely technical aspect, there are great problems in providing said continuously decreasing or increasing changes in the degrees of porosity in marked zones of the implant. The main object of the present invention is to solve this problem.

There is a need to be able to make available a range of implants which have different decreasing porosity functions in marked zones, i.e. there is a need for differently structured porosity arrangements on different implants. The invention also solves this problem. By virtue of having a range of implants with different porosity changes in one or more zones, an optimum implant can be used for the respective dental situation. It is known that the porosity affords a greater surface for union with surrounding bone. In the case of especially soft bone structures, it is of interest to be able to offer the large surfaces for union which high porosities afford. In some situations it may be of interest also to provide the outer surface of the attachment part with porosity.

The feature which can principally be regarded as characterizing an implant according to the invention is that the surfaces are provided with at least one zone in which the degree of finishing and/or the degree of roughness and/or the porosity is continuously changed.

In embodiments of the inventive concept, the implant has a single zone with continuously decreasing or increasing porosity. Some of the surface or surfaces, for example the surface of the attachment part, can be formed with a low, minimal porosity. In further illustrative embodiments, two or more zones can be arranged along the longitudinal and/or circumferential directions of the implant. In a preferred embodiment, each zone will take up a longitudinal or circumferential value which is 5% or more of the respective extent. The invention is preferably used in connection with implants having an outer thread or threads.

The feature which can principally be regarded as characterizing a method according to the invention is that the implant is applied wholly or partially in or near an electrolyte, and that the implant is subjected to cooling which is preferably substantial and that voltage is applied to an anode and cathode arrangement where the implant is arranged so that a current produced by the voltage is passed through the implant to establish said porosity. Liquid nitrogen can be used for cooling, and the implant can be connected to an anode included in the anode and cathode arrangement at a boundary surface in the container. The anode is situated in the nitrogen in the container and the cooling of the anode effected by the nitrogen is transmitted to the implant by means of its mechanical contact with the anode. The implant is immersed wholly or partially in electrolyte and a continuous transition zone is obtained by the fact that, in parts of the implant not immersed, the electrolyte is taken up in a decreasing amount along the height of the implant and by the fact that the decreasing amount gives rise to the continuous change in the porosity. In alternative embodiments, parts of the implant can be masked so that the electrolyte is prevented from gaining access to the masked portions and is thus prevented from forming porosities. Different sizes of porosities are determined inter alia by means of the electrolyte composition and/or changes in voltage and/or current.

The novel arrangement is characterized mainly by the fact that a number of implants are provided with different continuously decreasing changes in porosity in one or more zones and by the fact that the different implants in the range can be used to achieve optimum solutions to different dental situations.

Further embodiments of the implant, method and arrangement according to the above will be evident from the attached subclaims relating to the independent claims for the implant, method and arrangement, respectively.

By means of what has been proposed above it is possible to offer new types of implants which open up new approaches to and optimum solutions for dental situations. By means of the invention it is also possible, in an economically advantageous manner, to manufacture implants with porosities of the type in question in marked zones. It is therefore not necessary to use the abruptly changing zones in the known arrangements, with the different degrees of roughness/porosity which characterize the prior art. There are a great many possible variations for producing implants of this type and the novel method makes available a production technique which permits said variations in an advantageous manner. The invention also permits greater or lesser porosity on the surface of the attachment part if the priority is to eliminate risks of infection on the surface and to promote bone union (greater surfaces for incorporation of bone).

BRIEF DESCRIPTION OF THE DRAWINGS

The main characteristics of an implant, a method and an arrangement according to the invention will be described below with reference to the attached drawings, in which:

FIG. 4 is a side view and schematic representation showing an electrolyte used in the electrochemical process, and an anode and cathode arrangement arranged in this, FIG. 5 is a schematic representation, enlarged in relation to FIG. 4, showing the application of the implant in relation to a suitable cooling unit and electrolyte, and where the implant has been masked on parts of its length, FIG. 6 is a side view showing another masking in relation to the example in FIG. 5, FIG. 7 is a side view showing the implant with a number of different zones with continuously decreasing porosity and zones of very low porosity, FIG. 8 is a vertical section showing decreasing zones in the circumferential direction of the implant, FIG. 9 is a vertical section showing the application of the implant to an anode part which extends into the cooling unit/container unit according to FIG. 4, and where the porosity increases towards the free or lower end of the implant.

DETAILED DESCRIPTION

The varying or continuously modified porosity in the zone or zones concerned can be obtained in different ways. In the present case, an electrochemical method is preferably used which can be of a type known per se. As the electrochemical method which is described in the Swedish patent applications 9901971-3 and 9901974-7 is highly suitable for use in this context, reference is made to these patent applications which were filed by the same applicant as that of the present patent application. As will be evident from the electrochemical method already described, the oxide layer on the surface of the implant can be formed and varied by adjusting various parameters in the process, which parameters can include the composition of the electrolyte, the voltage and current in the anode and cathode arrangement used, the electrode geometry, the treatment time, etc. To obtain the features according to the present invention, the implant requires to be applied to and acted on by the electrolyte in the manner described below.

However, the electrochemical process will not be described in detail here, and instead reference is made to said patent applications.

Figure 1:
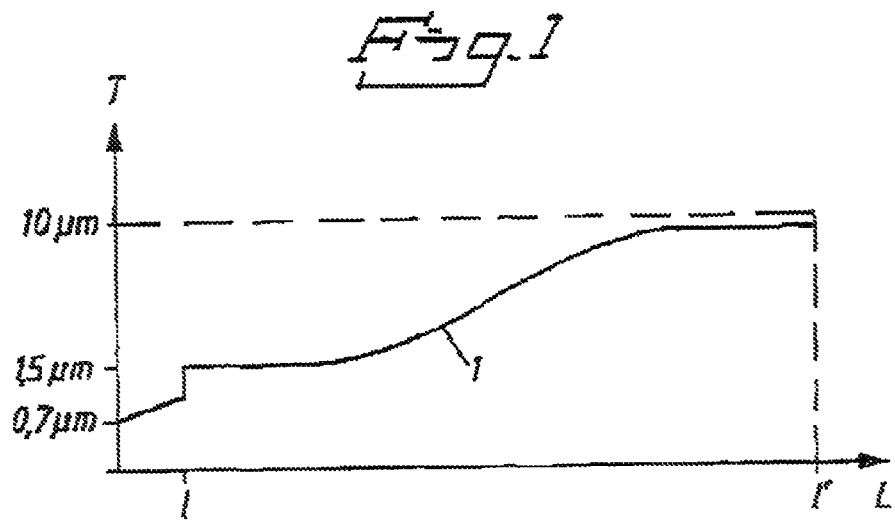
FIG. 1 is a diagram showing the porosity or roughness as a function of the implant length L, and a curve indicating a porosity continuously increasing towards one end of the implant.

In FIG. 1, a curve 1 indicates a continuously modified roughness/porosity along the length of an implant. The change here is assumed to be obtained along a zone or zones of the implant. In the present case, a low degree of roughness/porosity is used at one end of the implant, which low degree of roughness can have a value of 0.7 µm. After a predetermined extent along the implant, the roughness in this case changes distinctly to a value of 1.0 µm, for example. Thereafter, the roughness increases in the zone or zones in question up to a value of 1.5 µm. This increase represents a continuous change and can be linear and can have a progressiveness in accordance with the line of the curve 1.

Figure 2:
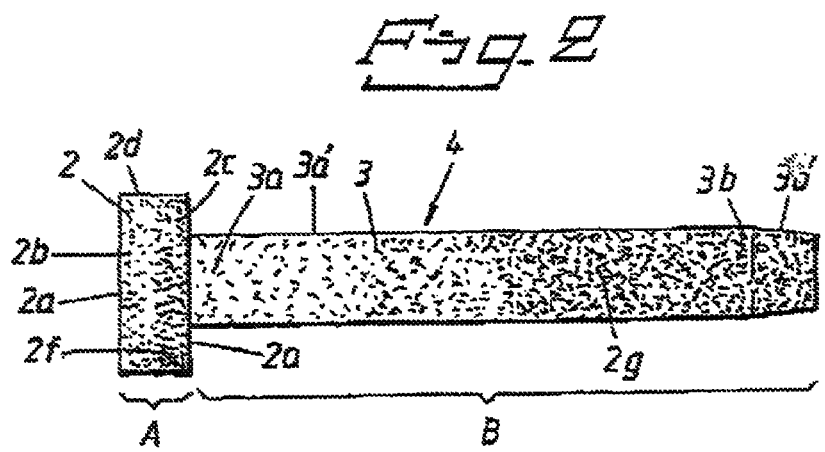
FIG. 2 is a side view showing an implant related to the diagram in FIG. 1, and where the implant has a certain degree of finishing on its left part (attachment part) and where the porosity or roughness increases as the curve rises in FIG. 1 towards the free end of the implant.

The implant shown diagrammatically in FIG. 2 is related to the diagram according to FIG. 1 such that a distance A on the implant corresponds to the distance 1 in the diagram. The length or distance B corresponds to the curve length 1 to 1'. As will be seen from FIG. 2, the distance A represents an attachment part 2 for a spacer element, and the distance B represents a hole-insert part 3 of an implant 4. The implant 4 has a design characteristic to the invention. In this case, the distances A and B form two different zones in which there is a continuous or progressive roughness/porosity. For example, the attachment part 2 can have less roughness/porosity along its length or a roughness/porosity which is lowest at an end surface 2a and increases gradually towards the bottom surface 2a'. The lower degree of roughness/porosity established at the end surface 2a is indicated by 2b, while the gently increasing roughness/porosity at the bottom surface 2a' is indicated by 2c. Thus, the outer surface 2d can be considered to have a low and gently increasing roughness/porosity viewed from the end surface 2a. According to the invention, the degree of roughness/porosity can be varied, and in one illustrative embodiment the outer surface 2d can be entirely without porosity markings or can have extremely low porosity, i.e. the outer surface 2d is very finely machined. In the illustrative embodiment, the extent B of the implant is arranged such that there is a single zone, in which zone therefore a low roughness/porosity is present at the upper end 3a of the hole-insert part 3 and a relatively high (cf. FIG. 1) roughness/porosity is present at the end 3b of the hole-insert part.

Figure 3:
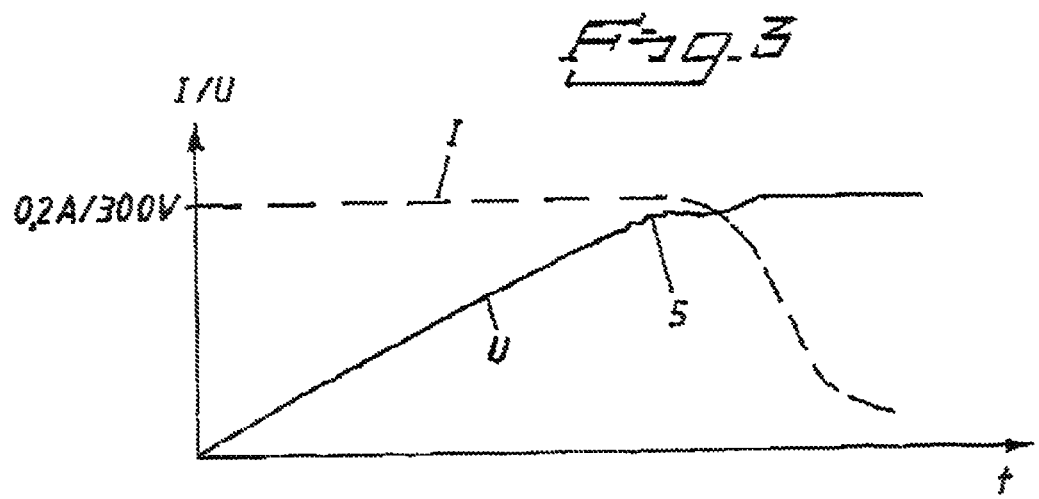
FIG. 3 is a diagram showing voltage and current parameters in an applied electrochemical process.

FIG. 3 shows typical current and voltage values in the electrochemical process (see also said Swedish patent applications). To establish high degrees of roughness and porosity, a current value of 0.2 ampere is used in this case, and the voltage value can extend up to a level of 300 volts, for example. The current curve is indicated by I and the voltage curve by U. The horizontal axis represents a time axis t. In accordance with the previously known method according to said Swedish patent applications, a certain spark formation occurs in the area 5 on the voltage curve U. The spark formation occurs along the whole of the implant surface and gives rise to pore formation and increased surface roughness.

FIG. 4 is a diagrammatic representation showing an electrolyte 15 used in the electrochemical process, and an anode and cathode arrangement applied in the latter. The anode 8 which can be formed by the implant itself or can consist of a part which is mechanically coupled to the implant 9 is connected to the positive potential 10 of an energy source 11. The positive connection of the anode and cathode arrangement is indicated by 13. The negative potential 12 of the energy source is correspondingly connected to the cathode 14 of the anode and cathode arrangement. As has been indicated in the figure, the lower parts 9a of the implant are dipped in the electrolyte 15. Capillary and other suction and evaporation phenomena mean that electrolyte is taken up in decreasing quantity-upwards and along the outer surface parts 9b of the implant which are situated above the immersed parts 9a of the implant. The effect of this is that the immersed parts 9a are exposed to a chemical treatment which gives a greater porosity than the porosity of those parts 9b which are situated above the parts 9a. This has the effect that a zone is obtained on the parts 9b where the porosity is continuously modified or decreases in the upward direction.

The kinetics of the electrochemical process can be controlled by varying the temperature of the implant. The porosity and surface roughness of the parts 9b can thus be regulated by cooling the implant. FIG. 4 shows a cooling arrangement 6 which in this case consists of a container 6a for liquid nitrogen 1. In the illustrative embodiment shown, the anode 8 of the anode and cathode arrangement is arranged in or extends through the interior 8 of the container and is in this way subjected to a cooling function exerted by the liquid nitrogen.

It will be appreciated from the above and from FIG. 5 that the position of the zone can be changed with the aid of the degree of immersion of the implant in the electrolyte 15. In FIG. 5, the degree of immersion can be adjusted in the directions of the arrows 16. It will also be appreciated that the suction forces along the surface 9c of the implant mean greater electrolyte accumulation 15a at the lower parts 9d of the implant than the electrolyte accumulation 15b at parts 9b which are situated higher up. The electrolyte can thus influence the implant with a greater amount of electrolyte at said lower parts 9d to than at the parts 9c situated higher up, which also indicates said continuous or progressive change or reduction of the porosity towards the upper parts of the implant. In accordance with the embodiment according to FIG. 5, masking functions are also used which correspond to those indicated in said Swedish applications. The maskings can consist of tube-shaped parts 17, 18 of Teflon, latex, etc.

Alternatively, lacquers can be used. The maskings are intended to prevent porosity occurring on the masked parts during the electrochemical process. In the present case, the tube part 17 or the like masks an area 9f which is situated under the spacer attachment part 2d. The last-mentioned part is in turn masked by the tube or the lacquer 18. Said areas 9f and 2d therefore have a very low porosity or no porosity at all, depending on previous treatment or working According to FIG. 6, it is also possible to use the masking function to form islands or areas 9g, 9h which extend across parts of the surfaces of the implant. In these areas 9g, 9h, the porosity continuously changes from the lower parts of the implant in the direction towards the upper parts of the implant. In this case the masking has been done with a tube, a lacquer, etc. 19 leaving the surface open for said areas. In the present case, the implant 9d is thus given a porosity which continuously increases or changes from the lower part up towards the masking 19, which increase or change merges into said areas 9g, 9h.

According to the invention, masking functions can thus be used, and during the total process of coating the implant 4 with one or more zones of decreasing or increasing porosity, the positions of the maskings can be rearranged or changed. According to FIG. 7, several zones C, D and E can be established along the longitudinal extent or height of the implant.

According to FIG. 8, different zones C', D' and E' can also be established in the circumferential direction where each zone, for example the zone 19, has a greater porosity at the end 19a than at the end 19b and the porosity continuously decreases within the zone.

It is also possible to influence the degree of roughness/porosity by mechanical working after the electrochemical treatment has been carried out.

FIG. 9 shows in more detail the mechanical connection between the implant 4 and the anode part 8 according to FIG. 4. The anode part 8 can have a recess for the spacer attachment part 2d of the implant, which recess is indicated by 8a. The size of the recess is adapted to the spacer attachment part so that the implant is secured in the anode part 8. This arrangement also provides masking for the outer surface 2d of the part 2. It will be evident from this embodiment that a large mechanical contact surface is present between the implant and the anode 8, which contact surface is established by means of the top surface 2a of the implant and the bottom surface 8a' of the recess 8a. The implant and the anode must be pressed against each other with forces F and F' respectively. Upon connection of the anode and cathode arrangement 13, 14 with a voltage according to the above, said porosity is established at the lower parts of the implant, while at the same time the implant is exposed to a very great cooling effect from the liquid nitrogen in the container 6a. The cooling function is thus established via the bottom part 6b of the cooling arrangement. The anode part 8 and the bottom part 6b can be sealed by means of a sealing ring 21 or the like.

Figure 10:
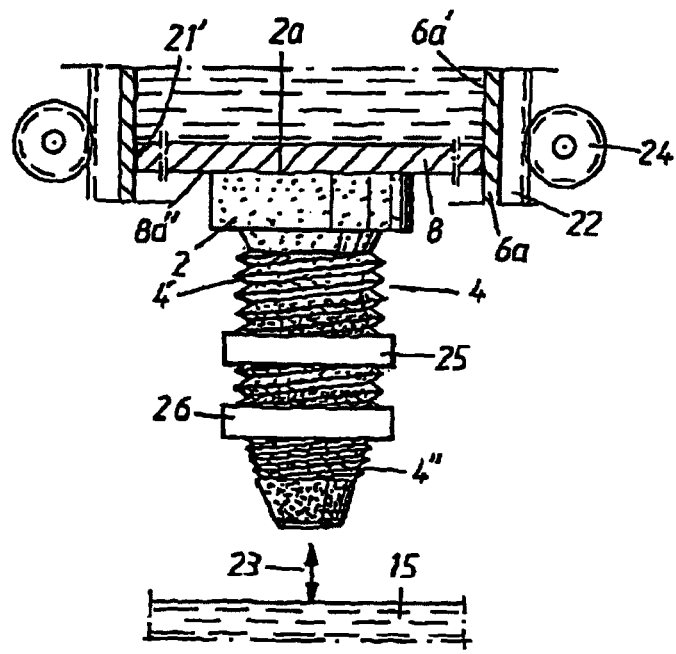
FIG. 10 is a vertical section/vertical view showing a further design of the connection of the implant to the cooling unit and maskings for establishing substantial porosity-free zones.

FIG. 10 shows another means of connection of the implant 4 to the anode part 8 which in this case does not have the recess (cf. 8a) indicated in FIG. 9. In this case, the top surface 2a of the spacer attachment member 2 is secured to the bottom surface 8a" of the anode by securing means of a suitable type. In this case, the anode part 8 is sealed off by sealing means or members 21' from the inner wall 6a' of the container 6a. The arrangement can be provided with guides 22 or equivalent acted on in the direction 23, for example by means of actuating members 24 which can consist of or comprise mechanical drive wheels (for example gear wheels). In this case, the implant 4 is provided with masks 25, 26 of the type indicated above. A characteristic of the zones is that the porosity is greatest at the bottom of each zone and decreases upwards to the spacer attachment part 2.

Figure 11:
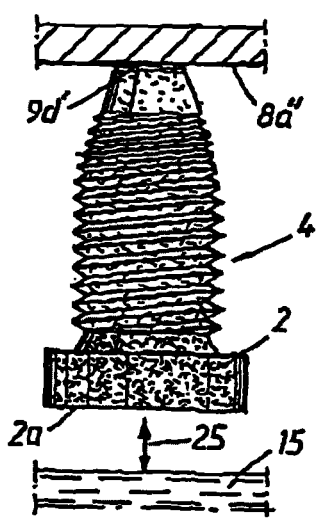
FIG. 11 is a vertical section/vertical view showing a reverse application to the cooling unit compared to the embodiment according to FIG. 10.

In FIG. 11, the implant is turned around compared to the case in FIG. 10. The free end surface 9d' of the implant is in this case secured in the recess 8a of the anode in the same way as in FIG. 10. Alternatively, the anode in this case can comprise a recess in the same way as in FIG. 9, which recess is adapted to the tip (free end) of the implant 4. In this case too, the implant, the anode, etc. are displaceable in the direction of the arrows 25 in order to provide for immersion in the electrolyte 15 to a greater or lesser extent. In this case, the coarse porosity is established at the end surface 2a of the spacer attachment part 2 and decreases towards the free end 9d' of the implant. In this case there is therefore only one zone.

Figure 12:
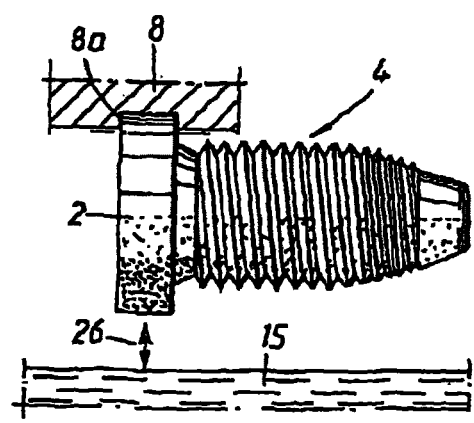
FIG. 12 is a vertical section/vertical view showing the application of the implant to the cooling unit with the implant lying in such a way that a varied porosity is obtained in the circumferential direction of the implant.

In the embodiment according to FIG. 12, the implant is in principle arranged horizontally in relation to the surface of the electrolyte 15. In this case too, the anode 8 has a recess 8a in which the spacer attachment part 2 is connected. The thus horizontally arranged implant can be immersed to a greater or lesser extent in the electrolyte 15 in the directions of the arrows 26. In this way, porosity of different sizes is present about the circumferential direction of the implant, cf. FIG. 8.

In accordance with the above, the implant itself can only form the anode in said anode and cathode arrangement. The implant extends through the bottom part 6b of the container 6 according to the example above. In FIG. 2, the outer surfaces of the hole-insert part have been indicated by 3a' and 3b'. The degrees of porosity have been symbolized by 2f and 2g, respectively. In FIG. 7, the length or height of the implant is indicated by H. A marked or extended zone, for example one of zones C, D or E, means that the extent of the zone in the direction H of the implant must be at least 5% of the value of H. Correspondingly, the decreasing porosity or porosities in the circumferential direction, for example the circumferential direction C' in FIG. 8, will assume a value of at least 5% of the total circumference 2h in said extended or marked zone. In FIG. 10, a first thread of a cylindrical portion is indicated by 4' and a thread on the tipped part of the implant is indicated by 4". The degree of immersion of the implant in the electrolyte 15 depends on where and how long the marked or extended zone for the continuously changed porosity is to be and/or on the degree of masking of the implant. According to the invention, it is also possible to provide a range of implants which are basically the same, but with different porosity changes within one or more marked zones, different zones, etc. Reference is made here to the different embodiments according to the above, where it is clear that implants can have different numbers of marked zones with different porosity changes, i.e. changes with different sizes of the porosities and different changes of these porosities. With such a range, it is possible to choose the implant which in the given dental situation is considered to give the best result or the most optimum result in said dental situation. The choice can be made on the basis of practical experience or by assigning different dental situations to different implants.

Figure 13:
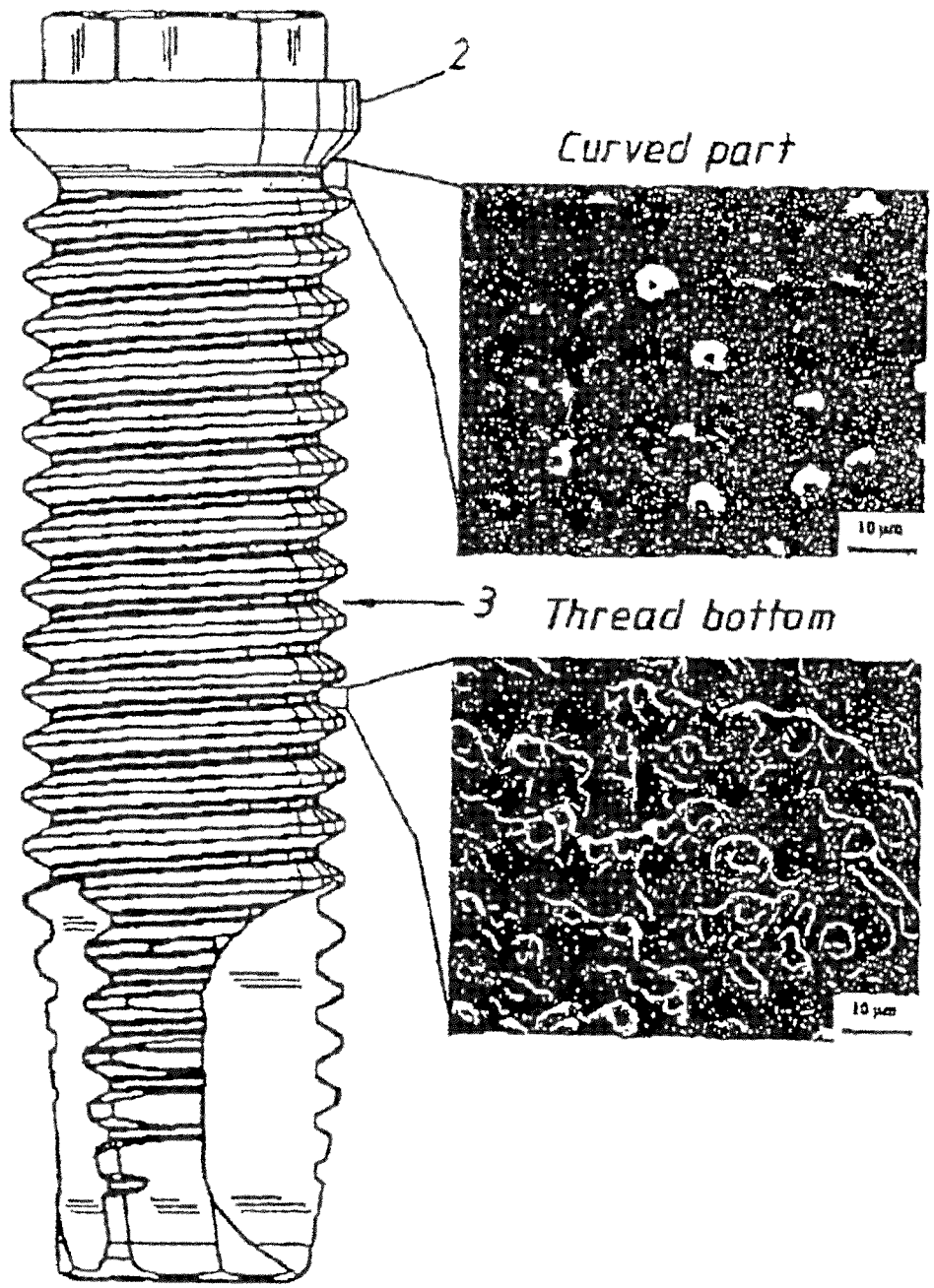
FIG. 13 shows an example of a dental implant produced according to the invention.

FIG. 13 shows an example of a dental implant of a type known per se (Branemark System®) which has been provided with a surface structure according to the invention. The implant is made of titanium and has a machined surface. The machined surface remains on the spacer attachment part 2, the flange, while the threaded part, the hole-insert part 3, has a roughness/porosity produced according to the above method and continuously decreasing along the length of the implant from the flange.

The figure also shows two enlargements taken on the threaded part, and on the curved part at the spacer attachment part, where the machined main surface has been acted on to a lesser extent by the electrolyte treatment.

The invention is not limited to the embodiment shown above by way of example, and instead it can be modified within the scope of the attached patent claims and the inventive concept.

What is claimed is:

1. A dental implant screw-comprising:
   an attachment part, and
   a threaded bone hole-insert part,
   wherein the threaded bone hole-insert part has surfaces comprising an oxide layer formed onto the dental implant screw, said oxide layer having different degrees of finishing, roughness or porosity,
   and further wherein said oxide layer comprises at least one zone having a continuously variable porosity along a longitudinal axis of the dental implant screw.

2. The dental implant screw according to claim 1, wherein said continuously variable porosity is obtained by an electrochemical method.

3. A dental implant screw-comprising:
   an attachment part, and
   a threaded bone hole-insert part,
   wherein the attachment part and the threaded bone hole-insert part have surfaces comprising oxide layers formed onto the dental implant screw, said oxide layers having different degrees of porosity,
   and further wherein said oxide layers comprise at least one zone having a continuously variable porosity along a longitudinal axis of the dental implant screw, and wherein said continuously variable porosity is obtained by an electrochemical method.

4. The dental implant screw according to claim 1, characterized in that the surfaces are provided with two or more zones (A, B, C, D, E) with continuously changed degrees of porosities.

5. The dental implant screw according to claim 1, wherein said at least one zone extends in a longitudinal direction of the dental implant screw.

6. The dental implant screw according to claim 1, characterized in that, in the case where there are two or more zones (A, B), these extend in the longitudinal direction of the implant.

7. The dental implant screw according to claim 1, characterized in that, in the case where there is one zone, the latter extends in the circumferential direction of the implant over a substantial part of the circumferential direction (C', D' or E') of the implant.

8. The dental implant screw according to claim 1, characterized in that, in the case where there are at least two zones (C', D', E'), these extend along parts of the circumferential direction (2h) of the implant.

9. The dental implant screw according to claim 1, wherein said at least one zone extends in a longitudinal direction of the dental implant screw for at least 5% of a length of the dental implant screw or wherein said at least one zone extends in a circumferential direction of the dental implant screw for at least 5% of a circumference of the dental implant screw.

10. The dental implant screw according to claim 1, characterized in that, in the case where there are two or more zones (C-E), two zones are arranged next to each other with the porosity modifications oriented towards or away from each other.

11. The dental implant screw according to claim 1, characterized in that a surface (2d) situated on the attachment part (2) has degree of finishing which is obtained by machining, and in that the degree of porosity increases continuously therefrom out towards the tip (9d) of the implant.

12. The dental implant screw according to claim 1, characterized in that the implants in the range have different continuously decreasing zones in the longitudinal and/or circumferential directions (H, 2b) of the implant.

13. The dental implant screw according to claim 1, further comprising a cylindrical threaded portion and a conical threaded portion at a tip of the dental implant screw.

14. The dental implant screw according to claim 1, wherein said oxide layers are formed by immersing said dental implant screw in an electrolyte bath.

15. The dental implant screw according to claim 1, wherein said at least one zone having a continuously variable porosity comprise adjacent first and second portions in which said continuously variable porosity gradually increases in the first portion and gradually decreases in the second portion.

16. The dental implant screw according to claim 1, wherein said oxide layers comprise titanium oxide layers.

* * * * *

UNITED STATES PATENT AND TRADEMARK OFFICE
CERTIFICATE OF CORRECTION

PATENT NO.         : 8,439,919 B2                                             Page 1 of 1
APPLICATION NO.    : 12/634466
DATED              : May 14, 2013
INVENTOR(S)        : Jan Hall It is certified that error appears in the above-identified patent and that said Letters Patent is hereby corrected as shown below:

On title page:
Under (63) Related U.S. Application Data: delete "PCT/SE01/00728" and substitute
-- PCT/SE01/000728 -- therefor.

In the Specification:
In Column 6:
Line 15: delete "nitrogen 1" and substitute -- nitrogen 7 -- therefor.

In column 8:
Line 33: delete "decreasing" and substitute -- increasing -- therefor.

In the Claims:
In column 9:
Line 3: delete "claim 1" and substitute -- claim 3 -- therefor.
Line 7: delete "claim 1" and substitute -- claim 3 -- therefor.
Line 10: delete "claim 1" and substitute -- claim 3 -- therefor.
Line 14: delete "claim 1" and substitute -- claim 3 -- therefor.
Line 19: delete "claim 1" and substitute -- claim 3 -- therefor.
Line 23: delete "claim 1" and substitute -- claim 3 -- therefor.

In column 10:
Line 1: delete "claim 1" and substitute -- claim 3 -- therefor.
Line 6: delete "claim 1" and substitute -- claim 3 -- therefor.
Line 11: delete "claim 1" and substitute -- claim 3 -- therefor.
Line 15: delete "claim 1" and substitute -- claim 3 -- therefor.
Line 18: delete "claim 1" and substitute -- claim 3 -- therefor.
Line 21: delete "claim 1" and substitute -- claim 3 -- therefor.
Line 26: delete "claim 1" and substitute -- claim 3 -- therefor.

Signed and Sealed this
Sixth Day of August, 2013

Teresa Stanek Rea
*Acting Director of the United States Patent and Trademark Office*